United States Patent
Hasumura et al.

(10) Patent No.: US 11,376,234 B2
(45) Date of Patent: Jul. 5, 2022

(54) AMMONIA METABOLISM PROMOTER

(71) Applicant: Kao Corporation, Tokyo (JP)

(72) Inventors: Takahiro Hasumura, Utsunomiya (JP); Shu Chen, Maoka (JP); Noriyasu Ota, Shimotsuke (JP); Mizuki Tsunakawa, Utsunomiya (JP); Yoshihiko Minegishi, Utsunomiya (JP)

(73) Assignee: Kao Corporation, Tokyo (JP)

( * ) Notice: Subject to any disclaimer, the term of this patent is extended or adjusted under 35 U.S.C. 154(b) by 129 days.

(21) Appl. No.: 16/619,704

(22) PCT Filed: May 31, 2018

(86) PCT No.: PCT/JP2018/020964
§ 371 (c)(1),
(2) Date: Dec. 5, 2019

(87) PCT Pub. No.: WO2018/225618
PCT Pub. Date: Dec. 13, 2018

(65) Prior Publication Data
US 2021/0228537 A1 Jul. 29, 2021

(30) Foreign Application Priority Data
May 31, 2018 (WO) .................. PCT/JP2018/020964

(51) Int. Cl.
*A61K 31/353* (2006.01)
*A61K 31/198* (2006.01)
*A61P 3/12* (2006.01)

(52) U.S. Cl.
CPC .......... *A61K 31/353* (2013.01); *A61K 31/198* (2013.01); *A61P 3/12* (2018.01)

(58) Field of Classification Search
CPC ........ A61K 31/353; A61K 31/198; A61P 3/12
See application file for complete search history.

(56) References Cited

U.S. PATENT DOCUMENTS

| | | | | |
|---|---|---|---|---|
| 8,609,735 | B2 * | 12/2013 | Ochiai | A61P 3/00 514/633 |
| 8,962,678 | B2 * | 2/2015 | Ota | A23L 33/175 514/456 |
| 2009/0197944 | A1 | 8/2009 | Ota et al. | |
| 2010/0292332 | A1 | 11/2010 | Ochiai et al. | |
| 2012/0196936 | A1 | 8/2012 | Kim et al. | |
| 2012/0259016 | A1 | 10/2012 | Jalan et al. | |
| 2013/0065843 | A1 | 3/2013 | Rupasinghe et al. | |

FOREIGN PATENT DOCUMENTS

| | | |
|---|---|---|
| EP | 3 636 257 A1 | 4/2020 |
| JP | 2000-239179 A | 9/2000 |
| JP | 2005-089384 A | 4/2005 |
| JP | 2007-191426 A | 8/2007 |
| JP | 2008-031148 A | 2/2008 |
| JP | 2011-132174 A | 7/2011 |
| JP | 2012-246294 A | 12/2012 |
| JP | 2013-505292 A | 2/2013 |
| JP | 2013-060406 A | 4/2013 |
| JP | 2013-526487 A | 6/2013 |
| JP | 2016-160216 A | 9/2016 |
| JP | 2018-203719 A | 12/2018 |
| WO | WO 2009/048148 A1 | 4/2009 |

OTHER PUBLICATIONS

Kromas et al., 7(7) World J. Hepatology 1007-1011 (2015) (Year: 2015).*
International Search Report (ISR) for PCT/JP2018/020964; I.A. fd May 31, 2018, dated Jul. 10, 2018 from the Japan Patent Office, Tokyo, Japan.
International Preliminary Report on Patentability (IPRP), Chapter I of the Patent Cooperation Treaty, including the Written Opinion, for PCT/JP2018/020964; I.A. fd May 31, 2018, dated Dec. 10, 2019, by the International Bureau of WIPO, Geneva, Switzerland.
Takeda, K et al., "Effects of citrulline supplementation on fatigue and exercise performance in mice," JNutr Sci Vitaminol (Tokyo) 2011;57(3):246-50.
Walker, V, "Ammonia toxicity and its prevention in inherited defects of the urea cycle," Diabetes Obes Metab. Sep. 2009;1 1(9):823-35. doi: 10.1111/j.1463-1326.2009.01054.x. Epub Jun. 16, 2009.
Meneguello, MO et al., "Effect of arginine, ornithine and citrulline supplementation upon performance and metabolism of trained rats," Cell Biochem Funct. Mar. 2003;21(1):85-91.
Li, C et al., "Green tea polyphenols control dysregulated glutamate dehydrogenase in transgenic mice by hijacking the ADP activation site," J Biol Chem. Sep. 30, 2011;286(39):34164-74. doi: 10.1074/jbc.M111.268599. Epub Aug. 3, 2011.
Singal, AS et al., "Green tea extract and catechin ameliorate chronic fatigue-induced oxidative stress in mice," J Med Food. 2005 Spring;8(1):47-52.
Sachdeva, AK et al., "Protective effect of epigallocatechin gallate in murine water-immersion stress model of chronic fatigue syndrome," Basic Clin Pharmacol Toxicol. Jun. 2010;106(6):490-6. doi: 10.1111/j. 1742-7843.2009.00525.x. Epub Jan. 18, 2010.
Sachdeva, AK et al., "Epigallocatechin gallate ameliorates behavioral and biochemical deficits in rat model of load-induced chronic fatigue syndrome" Brain Res Bull. Oct. 10, 2011;86(3-4):165-72. doi: 10.1016/j.brainresbull.2011.06.007. Epub Jul. 28, 2011.

(Continued)

*Primary Examiner* — Timothy R Rozof
(74) *Attorney, Agent, or Firm* — Sterne, Kessler, Goldstein & Fox P.L.L.C.

(57) ABSTRACT

A material which promotes ammonia metabolism in the body, as well as a material which has excellent ammonia metabolism improving effect and is effective for endurance enhancement and anti-fatigue are provided. An ammonia metabolism promoting agent, comprising catechins as an active ingredient. An agent for preventing or ameliorating hyperammonemia, hepatic encephalopathy or chronic fatigue syndrome, comprising catechins compound as an active ingredient. An ammonia metabolism promoting agent, an endurance enhancing agent and an anti-fatigue agent, comprising catechins, citrulline and arginine as active ingredients.

16 Claims, 5 Drawing Sheets

(56) References Cited

OTHER PUBLICATIONS

Tanaka, Masaaki, "Evaluation of functional food ingredient by fatigue animal model," Functional Food, 2010, vol. 3, No. 4, ISSN: 1882-3971, pp. 324-329.

Extended European search report (EESR) including the supplementary European search report and the European search opinion, for EP patent application No. 18813054.6, dated Feb. 2, 2021.

\* cited by examiner

[Figure 1]
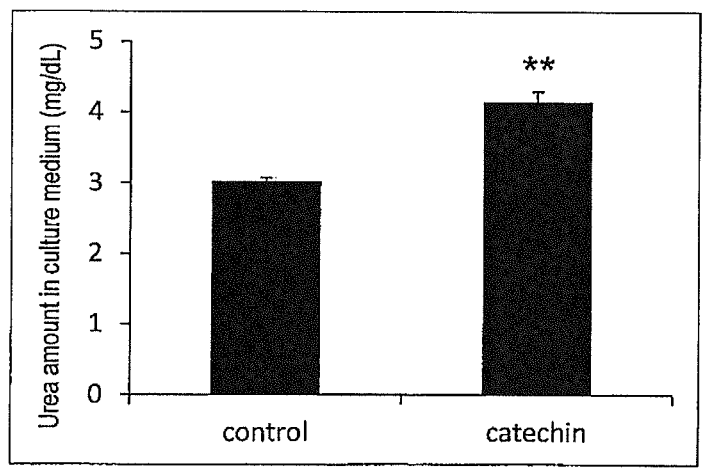
[Figure 2]
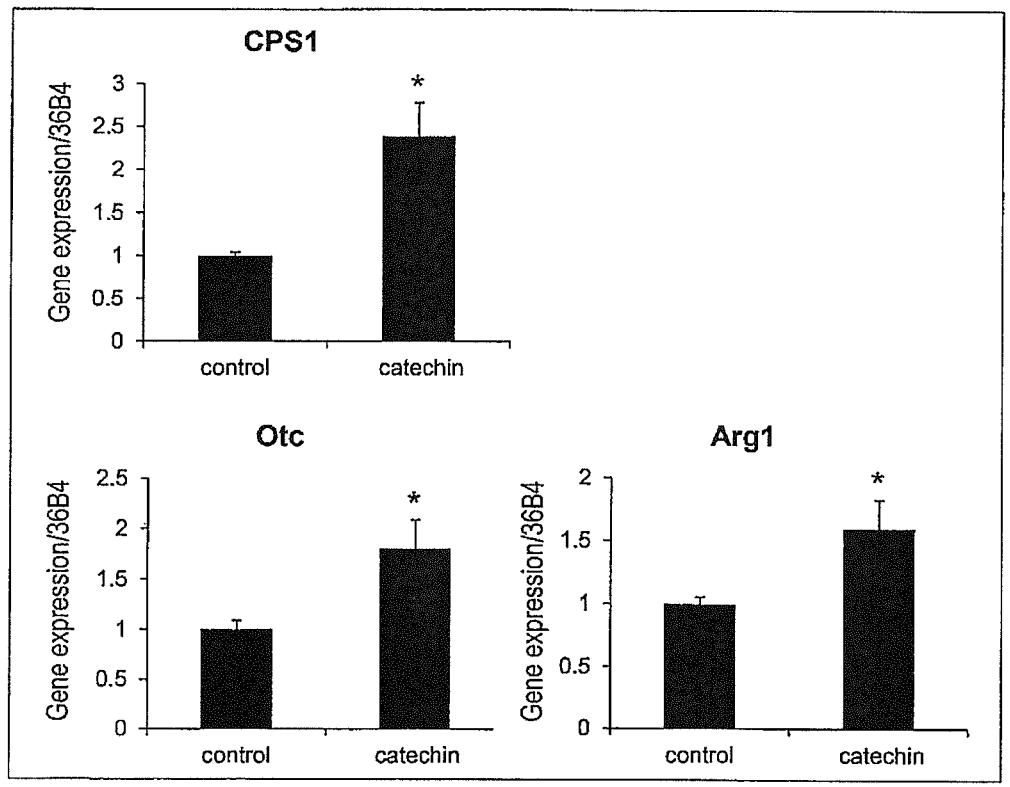

[Figure 3]
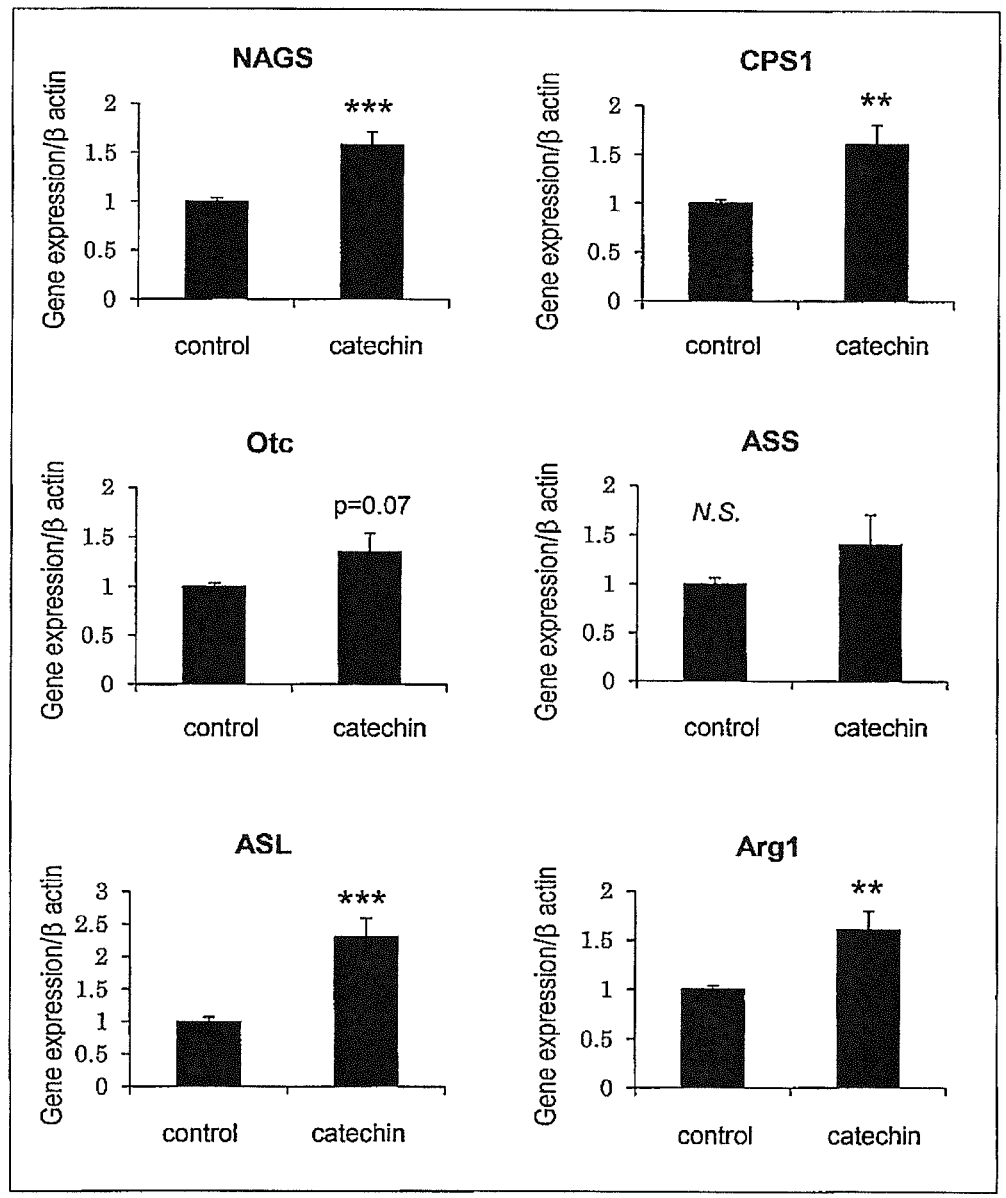

[Figure 4]
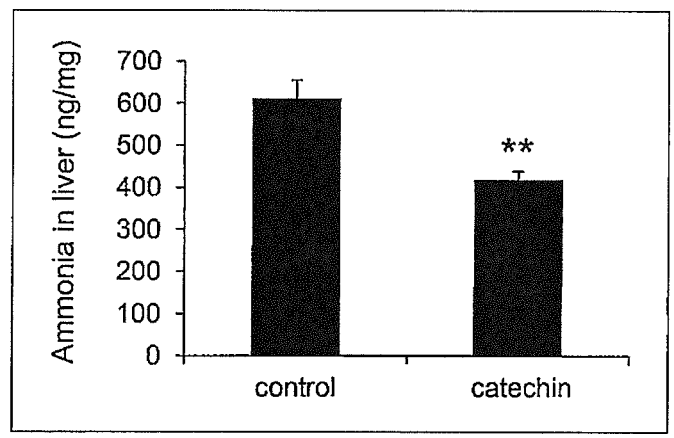
[Figure 5]
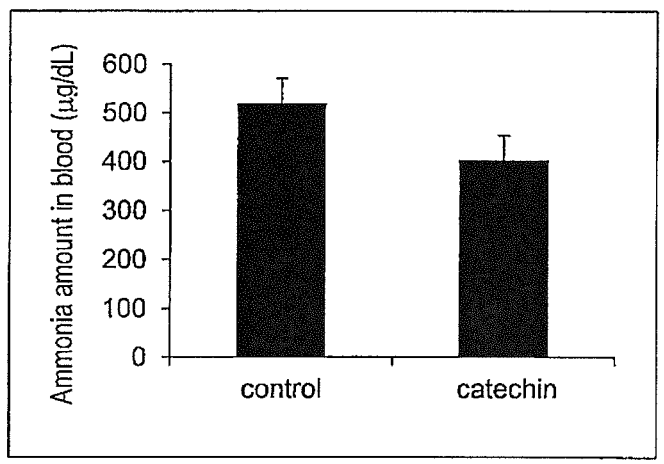

[Figure 6]
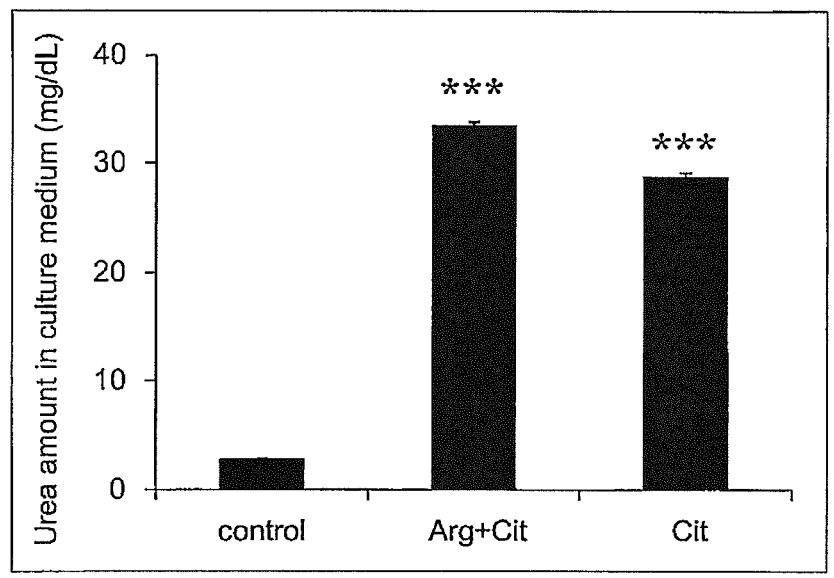
[Figure 7]
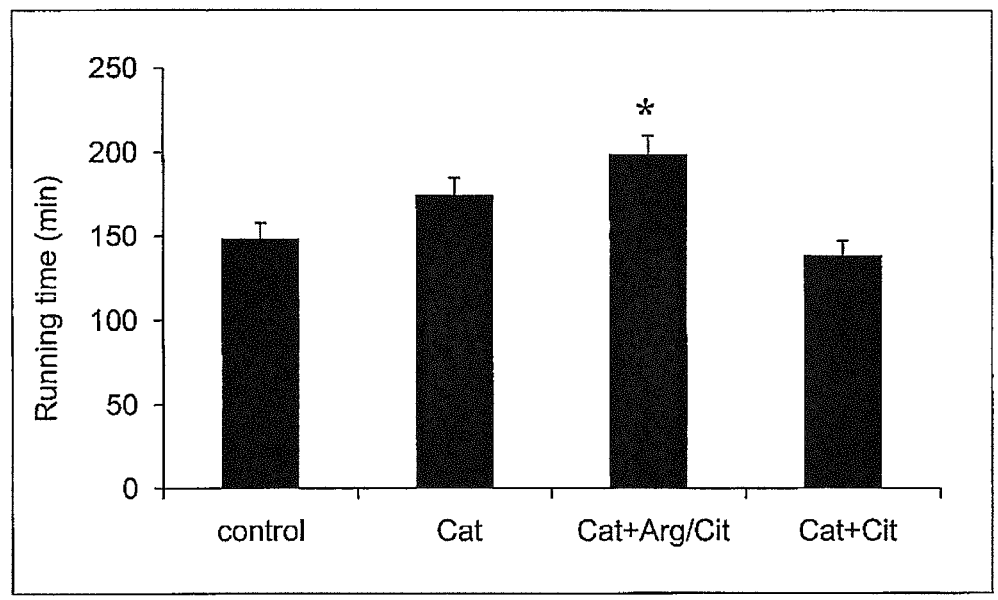

[Figure 8]
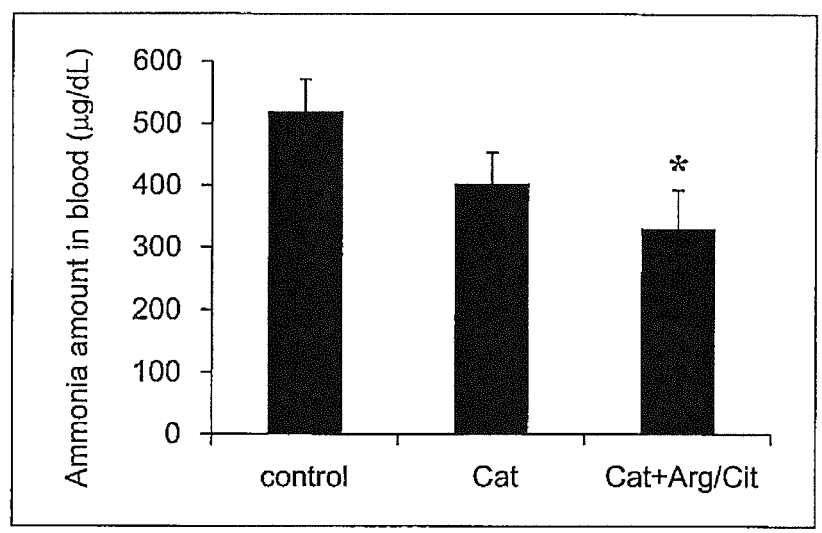

AMMONIA METABOLISM PROMOTER

FIELD OF THE INVENTION

The present invention relates to a material which promotes ammonia metabolism in the body. The present invention also relates to a material which promotes ammonia metabolism in the body and exerts an endurance enhancing effect and an anti-fatigue effect.

BACKGROUND OF THE INVENTION

Ammonia in the body is generated mainly in the process of protein metabolism or amino acid catabolism in muscle degradation by exercise or the like. Ammonia inhibits oxidation of pyruvate to acetyl-CoA to cause fatigue (see Non Patent Literature 1). It has also been known that ammonia causes nervous system hypofunction which is causative of central fatigue and promotes accumulation of lactic acid in muscles which leads to muscle fatigue (Patent Literature 1), and that hyperammonemia causes various disorders such as brain disorder (Non patent Literature 2). Ammonia accumulation in patients with chronic liver disease is thought to play an important role in the progression of hepatic encephalopathy and multiple organ failure (respiratory failure, cardiovascular failure and renal failure) (Patent Literature 2).

Ammonia in the body is converted to a harmless substance, urea by the urea cycle in the liver and excreted in the urine. Arginine, ornithine and citrulline are involved in the urea cycle in the liver which converts ammonia to a harmless substance, urea. It has been reported that the increase in blood ammonia is suppressed by ornithine, citrulline or arginine which is an amino acid involved in the urea cycle (Patent Literatures 3 and 4 and Non Patent Literature 1). In the body, citrulline is synthesized from ornithine, and citrulline is converted to arginine. It has been reported that ornithine suppresses the increase in blood ammonia and ameliorates fatigue (see Patent Literature 3). It has also been reported that ingestion of citrulline increases blood arginine and ameliorates brain fatigue (Patent Literatures 4 and 5).

Endurance is not only required in athletics, but is also essential for simple movements such as walking and running in our daily life and also for working in which muscular exertion is repeatedly performed. Reduced endurance causes difficulties in daily movements, especially in the elderly, and has a significant negative impact on quality of life (QOL). It is widely recognized that exercise training is effective in enhancing endurance. However, it is not easy at all to keep or enhance endurance by the exercise training due to the difficulty of securing time and keeping motivation and due to the risk of injury in the elderly.

Catechins have been previously reported as a component having an effect of enhancing endurance or preventing fatigue (Patent Literatures 6 and 7). However, there is no report on the effect of catechins on ammonia metabolism.

As components other than catechins, which have the effect of enhancing endurance or preventing fatigue, various amino acids such as ornithine (Patent Literature 3), citrulline (Non Patent Literature 1), combined use of citrulline and arginine (Patent Literature 4), combined use of arginine, ornithine and citrulline (Non Patent Literature 3) and the like have been reported.

(Patent Literature 1) JP-A-2000-239179
(Patent Literature 2) JP-A-2012-246294
(Patent Literature 3) JP-A-2011-132174
(Patent Literature 4) WO 2009/048148
(Patent Literature 5) JP-A-2013-060406
(Patent Literature 6) JP-A-2005-089384
(Patent Literature 7) JP-A-2008-031148
(Non Patent Literature 1) Takeda et al., J Nutr Sci Vitaminol, 2011, 57:246-250
(Non Patent Literature 2) Walker, Diabetes, Obesity and Metabolism, 2009, 11:823-835
(Non Patent Literature 3) Meneguello et al., Cell Biochem Funct, 2003, 21:85-91

SUMMARY OF THE INVENTION

The present invention provides an ammonia metabolism promoting agent comprising catechins as an active ingredient.

The present invention also provides an agent for preventing or ameliorating hyperammonemia, comprising catechins as an active ingredient.

The present invention also provides an agent for preventing or ameliorating hepatic encephalopathy, comprising catechins as an active ingredient.

The present invention also provides an agent for preventing or ameliorating chronic fatigue syndrome, comprising catechins as an active ingredient.

The present invention further provides an ammonia metabolism promoting agent, comprising catechins, citrulline and arginine as active ingredients.

The present invention further provides an endurance enhancing agent, comprising catechins, citrulline and arginine as active ingredients.

The present invention further provides an anti-fatigue agent, comprising catechins, citrulline and arginine as active ingredients.

BRIEF DESCRIPTION OF THE DRAWINGS

FIG. 1 is a graph showing an effect of catechins on urea production in primary cultured hepatocytes. Data are represented as AVG±SEM (N=3 to 6), ** $p<0.01$ (student's t-test), control: a control group, catechin; catechins-stimulated group.

FIG. 2 shows graphs showing effects of catechins on gene expression of ammonia metabolism related factors in primary cultured hepatocytes. Data are presented as AVG±SEM (N=4), * $p<0.05$ (student's t-test), control: a control group, catechin: catechins-stimulated group.

FIG. 3 shows graphs showing gene expression of ammonia metabolism related factors in the liver of catechins-ingested mice. Data are presented as AVG±SEM (N=8),  $p<0.01$, * $p<0.001$ (student's t-test), control: a control ingestion group, catechin: a catechins ingestion group.

FIG. 4 is a graph showing an effect of catechins on ammonia metabolism in the liver. Data are presented as AVG±SEM (N=8), ** $p<0.01$ (student's t-test), control: a control group, catechin: a catechins administered group.

FIG. 5 is a graph showing an effect of catechins on blood ammonia concentration. Data are presented as AVG±SEM (N=6 to 8), control: a control group, catechin: a catechins administered group.

FIG. 6 is a graph showing effects of citrulline and arginine on urea production in hepatocytes. Arg+Cit: arginine+citrulline; Cit: citrulline alone. Data are presented as AVG±SEM (N=3), *** $p<0.001$ (Dunnet test vs control).

FIG. 7 is a graph showing effects of catechins, citrulline and arginine on endurance. Cat: catechins alone; Cat+Arg/Cit: catechins+arginine+citrulline; Cat+Cit: catechins+citrulline. Data are presented as AVG±SEM (N=9 to 10), * $p<0.05$ (Dunnet test vs control).

FIG. 8 is a graph showing effects of catechins, citrulline and arginine on a blood ammonia concentration. Cat: catechins alone; Cat+Arg/Cit: catechins+arginine+citrulline. Data are presented as AVG±SEM (N=6 to 8), * p<0.05 (Fisher's LSD vs control).

DETAILED DESCRIPTION OF THE INVENTION (1. Definition)

All Patent Literatures, Non Patent Literatures and other publications cited herein are hereby incorporated by reference in their entirety.

As used herein, "non-therapeutic" is a concept which does not include any medical practice, that is, does not include a method for surgery, medical treatment or diagnosis of a human, more specifically a method for surgery, medical treatment or diagnosis of a human by a doctor, or a medical professional or a person who has been instructed by a doctor.

As used herein, "prevention" refers to preventing, suppressing or delaying the onset of a disease or condition in an individual, or reducing the risk of onset of a disease or condition in an individual. As used herein, "amelioration" refers to a change for the better of a disease or condition; prevention, suppression or delay of deterioration of a disease or condition; or reversal, prevention, suppression or delay of progression of a disease or condition.

As used herein, "exercise" refers to physical exercise in a broad sense including, for example, sports, training, athletics such as aerobic exercise (exercise in a narrow sense), working with muscular exertion, daily movements or the like. As used herein, "exercise", when used with respect to an athlete or a person performing an exercise in a narrow sense, can preferably mean an exercise in a narrow sense, whereas "exercise", when used with respect to the middle-aged or older, the elderly, the valetudinarian, the sick or a person who is recovering from a disease, it may preferably mean working or daily movements with muscle exertion.

As used herein, "endurance" refers to the endurance for the "exercise" described above, and "endurance enhancement" is a concept including enhancement of endurance and suppression of a reduction in endurance. As used herein, "anti-fatigue" refers to suppressing fatigue caused by the "exercise" or promoting recovery from the fatigue.

As used herein, "catechins" means at least one selected from the group of catechin (C), gallocatechin (GC), catechin gallate (Cg), gallocatechin gallate (GCg), epicatechin (EC), epigallocatechin (EGC), epicatechin gallate (ECg) and epigallocatechin gallate (EGCg). Among them, at least one selected from the group consisting of Cg, EGC and ECg is preferred, and at least one selected from the group consisting of Cg and EGC is more preferred. Therefore, the catechins used in the present invention preferably comprises at least one selected from the group of Cg, EGC and ECg and more preferably comprises at least one selected from the group consisting of Cg and EGC, and is still more preferably at least one selected from the group of Cg, EGC and ECg and is further preferably at least one selected from the group consisting of Cg and EGC. Alternatively, preferable examples of the catechins used in the present invention include one comprising Cg and EGC, one comprising Cg, EGC and ECg, a combination of Cg and EGC, a combination of Cg, EGC and ECg, and a combination of C, GC, Cg, GCg, EC, EGC, ECg and EGCg.

The catechins can be extracted, with water or hot water optionally with an extraction aid added, from tea leaves produced from leaves obtained from Camellia such as C. sinensis var. sinensis, C. sinensis var. assamica, Camellia sinensis var. sinensis cv. Yabukita or a hybrid thereof. The tea leaves include tea leaves of (1) green tea such as Sencha, Bancha, Gyokuro, Tencha or Kamairicha; (2) semi-fermented tea, collectively referred to as Oolong, such as Tieguanyin, Se Chung, Huangjin Gui or Wuyi tea; and (3) fermented tea, referred to as black tea, such as Darjeeling, Uva or Keemun. Extraction of the catechins from the tea leaves can be performed by a conventional method such as extraction with stirring. An organic acid or organic acid salt such as sodium ascorbate may be previously added to the water or hot water for extraction. If necessary, extraction may be performed in combination with a method of extraction under so-called non-oxidative atmosphere while removing dissolved oxygen with degassing by boiling or with aeration of an inert gas such as nitrogen gas.

Alternatively, a tea extract (including a concentrated or purified product thereof) may be used instead of extracting catechins directly from tea leaves. The concentrated product of a tea extract is, for example, a product obtained by concentrating an extract which is extracted from tea leaves with hot water or a water-soluble organic solvent, whereas the purified product of a tea extract is a product obtained by purifying the extract by using a solvent, a column or the like. Examples of the concentrated or purified product of a tea extract include products prepared by a method exemplified in detail in JP-A-59-219384, JP-A-4-20589, JP-A-5-260907, JP-A-5-306279 or the like. The tea extract and the concentrated or purified product thereof to be used may be commercially available products. Examples of the commercially available product include "POLYPHENON" from Mitsui Norin Co., Ltd., "Teaflan" from ITO EN, LTD., "Sunphenone" from Taiyo Kagaku Co., Ltd. and "SunOolong" from Suntory Ltd. The concentrated or purified product of a tea extract may be in the form of solid, liquid, slurry, and those dissolved or diluted in water, carbonated water or a tea extract extracted by a usual procedure or the like, without being particularly limited thereto.

The catechins in the present invention may be also derived from other raw materials other than tea leaves, such as a grape and processed products thereof (such as wine or a juice) or from cocoa beans and processed products thereof, or may be a chemically synthesized product.

The catechins of the present invention is preferably used in the form of a concentrated or purified product of a tea extract, and more preferably in the form of a concentrated or purified product of a green tea extract.

In the present invention, each of citrulline and arginine can be used in the form of a free form or a salt thereof. Each of citrulline and arginine may be any of an L-form, a D-form, a DL-form and mixtures thereof, but is preferably a L-form.

Examples of the salts of citrulline and arginine include an acid addition salt, a metal salt, an ammonium salt, an organic amine addition salt and an amino acid addition salt. Examples of the acid addition salt include an inorganic acid salt such as a hydrochloride, a sulfate, a nitrate or a phosphate, and an organic salt such as an acetate, a maleate, a fumarate, a citrate, a malate, a lactate, an α-ketoglutarate, a gluconate and a caprylate. Examples of the metal salt include an alkali metal salt such as a sodium salt or a potassium salt; an alkaline-earth metal salt such as a magnesium salt and a calcium salt; an aluminum salt and a zinc salt. Examples of the ammonium salt include ammonium and tetramethylammonium salts. Examples of the organic amine addition salt include salts of morpholine and piperidine. Examples of the amino acid addition salt include salts of glycine, phenylalanine, lysine, aspartic acid and glutamic acid.

The free forms of citrulline and arginine or salts thereof can be obtained by a method of isolation and purification from animals and plants comprising them, chemical synthesis, fermentative production and the like. Alternatively, commercially available products may be purchased.

(2. Ammonia Metabolism Promotion by Catechins)

In one aspect, the present invention relates to the provision of a material which promotes ammonia metabolism in the body. The present inventors have intensively studied and as a result, found that catechins have an excellent ammonia metabolism promoting effect in the body. According to the present invention, the catechins can promote ammonia metabolism in the body, and can ameliorate diseases or conditions caused by excessive accumulation of ammonia such as hyperammonemia, hepatic encephalopathy and chronic fatigue syndrome.

As is shown in the examples described below, catechins enhance gene expression of ammonia metabolism related factors in the liver cells and increase the amount of urea production (see FIGS. 1 to 3). In addition, ingestion of catechins reduce ammonia concentrations in the blood and the liver (see FIGS. 4 and 5). Therefore, according to the present invention, the catechins are used for promoting ammonia metabolism in the body.

The use of catechins for promotion of ammonia metabolism according to the present invention may include therapeutic use and non-therapeutic use. Examples of the non-therapeutic use include suppression of central fatigue associated with nervous system hypofunction caused by ammonia accumulation (see Patent Literature 1); and suppression of sleepiness or malaise caused by the central fatigue. Examples of the non-therapeutic use also include the provision of catechins, purporting to provide the above-described effects such as suppression of central fatigue, suppression of sleepiness or suppression of malaise, in order to administer the catechins to others or allow others to ingest the catechins not as a medical practice.

Examples of the therapeutic use include application to the prevention or amelioration of diseases or conditions caused by excessive accumulation of ammonia, such as chronic fatigue syndrome, hyperammonemia or hepatic encephalopathy. Hyperammonemia causes various conditions such as respiratory alkalosis, slurred speech, tremors, weakness, increased or decreased muscle tone, ataxia, hypothermia, seizure, brain edema, coma, brain stem compression, confusion with headache, nausea, vomiting, agitation, delusions and delirium, irritability, aggression; hyperactive, bizarre or self-injurious behavior; cognitive deficits, protein aversion, anorexia or delayed growth. Therefore, the prevention or amelioration of hyperammonemia according to the present invention may include the prevention or amelioration of the above described conditions caused by hyperammonemia.

Therefore, in one aspect, the present invention provides an ammonia metabolism promoting agent, comprising catechins as an active ingredient. The present invention also provides an agent for preventing or ameliorating hyperammonemia, comprising catechins as an active ingredient. The present invention also provides an agent for preventing or ameliorating hepatic encephalopathy, comprising catechins as an active ingredient. The present invention also provides an agent for preventing or ameliorating chronic fatigue syndrome, comprising catechins as an active ingredient.

In another aspect, the present invention provides use of catechins for producing an ammonia metabolism promoting agent. The present invention also provides use of catechins for producing an agent for preventing or ameliorating hyperammonemia, hepatic encephalopathy or chronic fatigue syndrome.

In one embodiment, the agent of the present invention may be composed essentially of catechins. In another embodiment, the agent of the present invention may be a composition at least comprising catechins.

In another aspect, the present invention provides use of catechins for promotion of ammonia metabolism. The present invention also provides use of catechins for preventing or ameliorating hyperammonemia, hepatic encephalopathy or chronic fatigue syndrome.

In further another aspect, the present invention provides catechins for use in promotion of ammonia metabolism. The present invention also provides catechins for use in preventing or ameliorating hyperammonemia, hepatic encephalopathy or chronic fatigue syndrome.

In the present invention, catechins can be used for both human and non-human animals. Examples of the non-human animals include non-human mammals, amphibians and fish. Examples of the non-human mammals include apes, the other primates, mice, rats, horses, cattle, pigs, sheep, dogs, cats, hamsters and companion animals.

In another aspect, the present invention provides a method for promoting ammonia metabolism in a subject. The present invention also provides a method for preventing or ameliorating hyperammonemia in a subject. The present invention also provides a method for preventing or ameliorating hepatic encephalopathy in a subject. The present invention also provides a method for preventing or ameliorating chronic fatigue syndrome in a subject. The methods comprise administering an effective amount of catechins to a subject. In a preferred embodiment, the administration is oral administration.

Examples of the subject to which the method of the present invention is applied include the above-described human and non-human animals in need of promotion of ammonia metabolism, or prevention of amelioration of hyperammonemia, hepatic encephalopathy or chronic fatigue syndrome, or suppression of central fatigue associated with nervous system hypofunction caused by ammonia accumulation, or suppression of sleepiness or malaise caused by the central fatigue.

Further examples of the subject include the above-described human and non-human animals in need of prevention or amelioration of a condition caused by the above-described hyperammonemia, such as respiratory alkalosis, slurred speech, tremors, weakness, increased or decreased muscle tone, ataxia, hypothermia, seizure, brain edema, coma, brain stem compression, confusion with headache, nausea, vomiting, agitation, delusions and delirium, irritability, aggression; hyperactive, bizarre or self-injurious behavior; cognitive deficits, protein aversion, anorexia or delayed growth, or the like.

Further examples of the subject include the above-described human and non-human animals in need of prevention or amelioration of a symptom or condition associated with an increase in blood ammonia level, such as slurred speech, lack of motivation, coma, impaired consciousness, fuzzy vision, developmental disorder, protein-induced vomiting or poor suckling in infants.

Alternatively, the method for promoting ammonia metabolism of the present invention may be an in vitro method. Examples of the subject to which the in vitro method is applied can include liver tissues and cultured hepatocytes (such as primary cultured hepatocytes) derived from the above-described human or non-human animals.

The effective amount of administration in the method of the present invention can be an amount capable of achieving promotion of ammonia metabolism in a subject. The ammonia metabolism level can be evaluated by measuring the blood ammonia concentration or the urea production amount with respect to a subject. For example, the effective amount may be an amount which statistically significantly increases the ammonia metabolism level in the group receiving catechins as compared to the non-administration group. For example, the effective amount may be also an amount which reduces the blood ammonia concentration in the population receiving catechins to 90% or less and preferably 80% or less of that in the non-administration group. For example, the effective amount may be also an amount which statistically significantly increases the amount of urea production in cultured hepatocytes (such as primary cultured hepatocytes) as compared to the non-administration group or increases the amount of urea production in cultured hepatocytes (such as primary cultured hepatocytes) to 120% or more and preferably 130% or more of that in the non-administration group.

Alternatively, the ammonia metabolism level can be evaluated by measuring the expression levels of ammonia metabolism related factors in the liver. Examples of the ammonia metabolism related factor include at least one selected from the group consisting of NAGS (N-acetylglutamate synthase), CPS1 (carbamoyl phosphate synthase-1), Otc (ornithine transcarbamoylase), ASS (argininosuccinate synthase), ASL (argininosuccinate lyase) and Arg1 (arginase-1). The above factors are enzymes involved in ammonia metabolism in the liver, and an increase in the expression level of each factor promotes ammonia metabolism in the liver. The expression level of each of the above-mentioned factors can be measured by any known means, such as by measurement of the expression level of the gene (mRNA) of the factor by real-time PCR. Therefore, in one embodiment, the effective amount for administration in the method of the present invention may be an amount which statistically significantly increases the expression level of ammonia metabolism related factor in the liver tissue or cultured hepatocytes (such as primary cultured hepatocytes) as compared to the non-administration group.

In the present invention, catechins can be used as an active ingredient for imparting the function of promoting ammonia metabolism or as an active ingredient for imparting the function of preventing or ameliorating diseases or conditions caused by excessive accumulation of ammonia, such as hyperammonemia, hepatic encephalopathy or chronic fatigue syndrome, to a drug, a quasi drug, a food and beverage (including a food and beverage for non-human animals) or the like.

The drug (including quasi drug) is a drug for promotion of ammonia metabolism; or a drug for preventing or ameliorating diseases or conditions caused by excessive accumulation of ammonia, such as hyperammonemia, hepatic encephalopathy, or chronic fatigue syndrome. The drug comprises catechins as an active ingredient for imparting the function. The drug may further comprise a pharmaceutically acceptable carrier, or another active ingredient, a pharmacological component or the like if necessary, as long as the functions of the active ingredients are not lost.

The administration mode of the drug (including quasi drug) may be either an oral administration or a parenteral administration, but an oral administration is preferred. The dosage form of the drug is any dosage form which can be administered orally or parenterally, without being particularly limited thereto, such as an injection, a suppository, an inhalant, a transdermal agent, various topical agents, a tablet, a capsule, a granule, a powder, a solution or a syrup. The formulations in various dosage forms can be also prepared by appropriately combining a catechin compound with a pharmaceutically acceptable carrier (such as an excipient, a binder, a filler, a disintegrant, a surfactant, a lubricant, a dispersant, a buffer, a preservative, a flavoring agent, a perfume, a coating agent or a diluent), another pharmaceutically active ingredient and the like, according to a conventional method.

The food and beverage is a food and beverage for providing the function of promoting ammonia metabolism; suppressing central fatigue associated with nervous system hypofunction caused by ammonia accumulation; or suppressing sleepiness or malaise caused by the central fatigue; or the like, and it comprises catechins as an active ingredient for the function. The food and beverage includes a food and beverage for patients as well as a food and beverage with health claims such as a food and beverage with nutrient function claims, a food and beverage for specified health uses or a food and beverage with function claims, which are based on the concept of such a function as promotion of ammonia metabolism, suppression of central fatigue, suppression of sleepiness, suppression of malaise or the like, and on which the concept is indicated as needed.

The food and beverage may be in the form of solid, semi-solid or liquid (such as a drink). Examples of the food and beverage include breads, noodles, rice, confectionaries such as cookies, jellies, dairy products, soups, frozen foods, instant foods, modified starch products, processed fish meat products, other processed foods, seasonings, nutritional supplements and drinks such as tea and coffee drinks, fruit drinks, carbonated drinks and jelly-like drinks, as well as ingredients thereof. Alternatively, the food and beverage may be a supplement in the form of an oral formulation such as a tablet, a capsule, a granule, a powder, a solution or a syrup.

The food and beverage can be prepared by appropriately combining catechins with any food and beverage material or any additive which is acceptable in a food and beverage (such as a solvent, a softener, an oil, an emulsifier, a preservative, a flavor, a sweetener, a stabilizer, a coloring agent, an ultraviolet absorber, an antioxidant, a moisturizing agent, a thickener, an adhesive, a dispersing agent or a wetting agent), according to a conventional method.

The content of catechins in the drug (including quasi drug) is not particularly limited, but is preferably 0.01% by mass or more, more preferably 0.05% by mass or more and still more preferably 0.1% by mass or more, and preferably 10% by mass or less, more preferably 5% by mass or less, still more preferably 2.5% by mass or less and further preferably 1% by mass. Examples of the content also include from 0.01 to 10% by mass, from 0.01 to 5% by mass, from 0.01 to 2.5% by mass, from 0.01 to 1% by mass, from 0.05 to 10% by mass, from 0.05 to 5% by mass, from 0.05 to 2.5% by mass, from 0.05 to 1% by mass, from 0.1 to 10% by mass, from 0.1 to 5% by mass, from 0.1 to 2.5% by mass and from 0.1 to 1% by mass can be mentioned.

The content of a catechins in the food and beverage is not particularly limited, but is preferably 0.01% by mass or more, more preferably 0.05% by mass or more and still more preferably 0.1% by mass or more, and preferably 5% by mass or less, more preferably 2.5% by mass or less and still more preferably 1% by mass or less. Examples of the content also include from 0.01 to 5% by mass, from 0.01 to 2.5% by mass, from 0.01 to 1% by mass, from 0.05 to 5% by mass, from 0.05 to 2.5% by mass, 0.05 to 1% by mass, from 0.1 to 5% by mass, from 0.1 to 2.5% by mass and from 0.1 to 1% by mass can be mentioned.

In the present invention, the dosages and dosing regimens of catechins may be appropriately determined by those skilled in the art according to the species, body weight, sex, age, condition or other factors of the particular subject. When orally administered, examples of the daily dosages per adult of the catechins according to the present invention are preferably from 100 to 3,000 mg/60 kg body weight, more preferably from 250 to 2,000 mg/60 kg body weight and still more preferably from 250 to 1,000 mg/60 kg body weight. The above dosage is preferably administered once a day, or in divided doses twice or three or more times a day.

(3. Ammonia Metabolism Promotion and Endurance Enhancement by Combined Use of Catechins, Citrulline and Arginine)

In another aspect, the present invention relates to the provision of a material which has excellent ammonia metabolism promoting effect and is effective for endurance enhancement and anti-fatigue. The present inventors found that use of catechins in combination with citrulline and arginine provides a remarkably higher ammonia metabolism promoting effect and endurance improving effect as compared with catechins alone or a combination of citrulline and arginine alone. The use of catechins in combination with citrulline and arginine according to the present invention promotes ammonia metabolism in the body and provides alleviation of fatigue and endurance enhancement. By the combined use according to the present invention, in the valetudinarian or the middle-aged or older who suffers from reduced endurance and fatigue, in the elderly or in a person who needs enhancement in motor function (such as athletes), exercise endurance can be enhanced or fatigue by exercise can be alleviated.

In the present invention, by combined use of three components of catechins, citrulline and arginine, a remarkably higher ammonia metabolism promoting effect and endurance enhancing effect are achieved as compared to application of one of them alone or a combination of citrulline and arginine alone. In the present invention, the three components of catechins, citrulline and arginine may be administered simultaneously as one composition comprising the three components or each component may be administered separately, as long as they can cooperatively act in vivo.

Therefore, in one aspect, the present invention provides an ammonia metabolism promoting agent, comprising catechins, citrulline and arginine as active ingredients. The present invention further provides an endurance enhancing agent, comprising catechins, citrulline and arginine as active ingredients. The present invention further provides an anti-fatigue agent, comprising catechins, citrulline and arginine as active ingredients.

In another aspect, the present invention provides use of catechins, citrulline and arginine for producing an ammonia metabolism promoting agent, an endurance enhancing agent and an anti-fatigue agent.

In a preferred embodiment, each of the ammonia metabolism promoting agent, the endurance enhancing agent and the anti-fatigue agent of the present invention is a composition at least comprising the three components of catechins, citrulline and arginine. In one embodiment, the agent of the present invention may be composed essentially of catechins, citrulline and arginine.

In another aspect, the present invention also provides use of catechins, citrulline and arginine for promotion of ammonia metabolism, endurance enhancement or anti-fatigue. In a preferred embodiment, the catechins, citrulline and arginine are used in the form of a composition comprising them.

In further another aspect, the present invention provides a composition comprising catechins, citrulline and arginine for use in promotion of ammonia metabolism, endurance enhancement or anti-fatigue.

The use of the three components of catechins, citrulline and arginine according to the present invention may include therapeutic use and non-therapeutic use. Examples of the non-therapeutic use include administering or ingesting catechins, citrulline and arginine, not as a medical practice, but for the purpose of obtaining a health promotion effect such as alleviation of fatigue by physical activity in the daily life, endurance enhancement or fatigue alleviation in working with muscular exertion, endurance enhancement during exercise in a narrow sense, or promotion of recovery from fatigue during or after exercise in a narrow sense. Examples of the non-therapeutic use also include the provision of catechins, citrulline and arginine, purporting to provide the above-described health promotion effect, in order to administer the catechins, citrulline and arginine to others or allow others to ingest the catechins, citrulline and arginine not as a medical practice.

Examples of the therapeutic use include application for the prevention or amelioration of diseases or conditions caused by excessive accumulation of ammonia, such as chronic fatigue syndrome, hyperammonemia and hepatic encephalopathy.

In the present invention, catechins, citrulline and arginine can be used for both human and non-human animals. Examples of the non-human animals include non-human mammals, amphibians and fish. Examples of the non-human mammals include apes, other primates, mice, rats, horses, cattle, pigs, sheep, dogs, cats, hamsters and companion animals In another aspect, the present invention provides a method for promoting ammonia metabolism in a subject. The present invention also provides a method for enhancing endurance in the subject. The present invention also provides a method for anti-fatigue in a subject. The methods comprise administering effective amounts of catechins, citrulline and arginine to a subject. In a preferred embodiment, a composition comprising catechins, citrulline and arginine is administered. In another preferred embodiment, the administration is oral administration.

Examples of the subject to which the method of the present invention is applied include the above-described human and non-human animals in need of promotion of ammonia metabolism, endurance enhancement, anti-fatigue, or in need of prevention or amelioration of diseases or conditions caused by excessive accumulation of ammonia, such as chronic fatigue syndrome, hyperammonemia or hepatic encephalopathy.

Further examples of the subject include the above-described human and non-human animals in need of alleviation of fatigue by physical activity in the daily life, endurance enhancement or fatigue alleviation in working with muscular exertion, endurance enhancement during exercise in a narrow sense, or promotion of recovery from fatigue during or after exercise in a narrow sense, or the like.

Further examples of the subject include the above-described human and non-human animals in need of prevention or amelioration of a condition caused by hyperammonemia, such as respiratory alkalosis, slurred speech, tremors, weakness, increased or decreased muscle tone, ataxia, hypothermia, seizure, brain edema, coma, brain stem compression, confusion with headache, nausea, vomiting, agitation, delusions and delirium, irritability, aggression; hyperactive, bizarre or self-injurious behavior; cognitive deficits, protein aversion, anorexia or delayed growth, or the like.

Further examples of the subject include the above-described human and non-human animals in need of suppression of central fatigue associated with nervous system hypofunction caused by ammonia accumulation; and suppression of sleepiness or malaise caused by the central fatigue.

Further examples of the subject include the above-described human and non-human animals in need of prevention or amelioration of a symptom or condition associated with an increase in blood ammonia concentration, such as slurred speech, lack of motivation, coma, impaired consciousness, fuzzy vision, developmental disorder, protein-induced vomiting or poor suckling in infants.

Alternatively, the method for promoting ammonia metabolism of the present invention may be an in vitro method. Examples of the subject to which the in vitro method is applied can include liver tissues and cultured hepatocytes (such as primary cultured hepatocytes) derived from the above-described human or non-human animals.

The effective amount for administration in the method of the present invention may be an amount which can achieve promotion of ammonia metabolism in a subject, or an amount which can achieve endurance enhancement or anti-fatigue. The ammonia metabolism level can be evaluated by measuring the blood ammonia concentration or the amount of urea production in a subject. The endurance and fatigue resistance can be evaluated by a treadmill test or the like. In one embodiment, the effective amount may be an amount that statistically significantly increases the ammonia metabolism level in the group receiving the three components of catechins, citrulline and arginine as compared to the non-administration group. In another embodiment, the effective amount may be also an amount which reduces the blood ammonia concentration in the population receiving the three components to 90% or less and preferably 80% or less of that in the non-administration group. In another embodiment, the effective amount can be also an amount that statistically significantly reduces the blood ammonia concentration in the population receiving the three components as compared to the non-administration group. In further another embodiment, the effective amount may be also an amount which statistically significantly increases the amount of urea production in the population receiving the three components to two times or more and preferably three times or more that in the non-administration group. In further another embodiment, the effective amount may be an amount that statistically significantly prolongs the treadmill running time in the population receiving the three components as compared to the non-administration group.

In the present invention, catechins, citrulline and arginine can be used as active ingredients for imparting the function of promotion of ammonia metabolism, endurance enhancement or anti-fatigue or as active ingredients for preventing or ameliorating diseases or conditions caused by excessive accumulation of ammonia, such as chronic fatigue syndrome, hyperammonemia or hepatic encephalopathy, to a drug, a quasi drug or a food and beverage (including a food and beverage for non-human animals).

The drug (including quasi drug) is a drug for promotion of ammonia metabolism, endurance enhancement or anti-fatigue, or a drug for preventing or ameliorating diseases or conditions caused by excessive accumulation of ammonia, such as chronic fatigue syndrome, hyperammonemia or hepatic encephalopathy. The drug comprises catechins, citrulline and arginine as active ingredients for imparting the function. The drug may further comprise a pharmaceutically acceptable carrier, or another active ingredient, a pharmacological component or the like if necessary, as long as the functions of the active ingredients are not lost. The drug may be provided as one composition comprising catechins, citrulline and arginine, or may be provided as a combination of a plurality of compositions comprising one or two of them.

The administration mode of the drug (including quasi drug) may be either an oral administration or a parenteral administration, but an oral administration is preferred. The dosage form of the drug is any dosage form which can be administered orally or parenterally, without being particularly limited thereto, such as an injection, a suppository, an inhalant, a transdermal agent, various topical agents, a tablet, a capsule, a granule, a powder, a solution or a syrup. The formulations in various dosage forms can be also prepared by appropriately combining catechins, citrulline and arginine with a pharmaceutically acceptable carrier (such as an excipient, a binder, a filler, a disintegrant, a surfactant, a lubricant, a dispersant, a buffer, a preservative, a flavoring agent, a perfume, a coating agent or a diluent), another pharmaceutically active ingredient and the like, according to a conventional method.

The food and beverage is a food and beverage for providing the function of promotion of ammonia metabolism, endurance enhancement or anti-fatigue, and comprises catechins, citrulline and arginine as active ingredients. The food and beverage includes a food and beverage for the sick as well as a food and beverage with health claims such as a food and beverage with nutrient function claims, a special health food and beverage or a food and beverage with functional claims, which are based on the concept of such a function of promotion of ammonia metabolism, endurance enhancement or prevention or amelioration of anti-fatigue, and on which the concept is indicated as needed.

The food and beverage may be in the form of solid, semi-solid or liquid (such as a drink). Examples of the food and beverage include breads, noodles, rice, confectionaries such as cookies, jellies, dairy products, soups, frozen foods, instant foods, modified starch products, processed fish meat products, other processed foods, seasonings, nutritional supplements and drinks such as tea and coffee drinks, fruit drinks, carbonated drinks and jelly-like drinks, as well as ingredients thereof. Alternatively, the food and beverage may be a supplement in the form of an oral formulation such as a tablet, a capsule, a granule, a powder, a solution or a syrup. The food and beverage may be provided as one composition comprising catechins, citrulline and arginine, or may be provided as a combination of a plurality of compositions comprising one or two of them.

The food and beverage can be prepared by appropriately combining catechins, citrulline and arginine with any material for a food and beverage or any additive which is acceptable in a food (such as a solvent, a softener, an oil, an emulsifier, a preservative, a flavor, a sweetener, a stabilizer, a coloring agent, an ultraviolet absorber, an antioxidant, a moisturizing agent, a thickener, an adhesive, a dispersing agent or a wetting agent), according to a conventional method.

The content of catechins in the drug (including quasi drug) is not particularly limited, but is preferably 0.01% by mass or more, more preferably 0.05% by mass or more and still more preferably 0.1% by mass or more, and preferably 10% by mass or less, more preferably 5% by mass or less, still more preferably 2.5% by mass or less and further preferably 1% by mass or less. Examples of the content also include from 0.01 to 10% by mass, from 0.01 to 5% by mass, from 0.01 to 2.5% by mass, from 0.01 to 1% by mass, from 0.05 to 10% by mass, from 0.05 to 5% by mass, from 0.05 to 2.5% by mass, from 0.05 to 1% by mass, from 0.1 to 10% by mass, from 0.1 to 5% by mass, from 0.1 to 2.5% by mass and from 0.1 to 1% by mass.

The content of catechins in the food and beverage is not particularly limited, but is preferably 0.01% by mass or more, more preferably 0.05% by mass or more and still more preferably 0.1% by mass or more, and preferably 5% by mass or less, more preferably 2.5% by mass or less and still more preferably 1% by mass or less. Examples of the content also include from 0.01 to 5% by mass, from 0.01 to 2.5% by mass, from 0.01 to 1% by mass, from 0.05 to 5% by mass, from 0.05 to 2.5% by mass, from 0.05 to 1% by mass, from 0.1 to 5% by mass, from 0.1 to 2.5% by mass and from 0.1 to 1% by mass.

The content of citrulline in the drug (including quasi drug) is not particularly limited, but is, in terms of free form of citrulline, preferably 0.01% by mass or more, more preferably 0.05% by mass or more and still more preferably 0.1% by mass or more, and preferably 10% by mass or less, more preferably 5% by mass or less, still more preferably 2.5% by mass or less and further preferably 1% by mass or less. Examples of the content also include from 0.01 to 10% by mass, from 0.01 to 5% by mass, from 0.01 to 2.5% by mass, from 0.01 to 1% by mass, from 0.05 to 10% by mass, from 0.05 to 5% by mass, from 0.05 to 2.5% by mass, from 0.05 to 1% by mass, from 0.1. to 10% by mass, from 0.1 to 5% by mass, from 0.1 to 2.5% by mass and from 0.1 to 1% by mass.

The content of citrulline in the food and beverage is not particularly limited, but is, in terms of free form of citrulline, preferably 0.01% by mass or more, more preferably 0.05% by mass or more and still more preferably 0.1% by mass or more, and preferably 5% by mass or less, more preferably 2.5% by mass or less and still more preferably 1% by mass or less. Examples of the content also include from 0.01 to 5% by mass, from 0.01 to 2.5% by mass, from 0.01 to 1% by mass, from 0.05 to 5% by mass, from 0.05 to 2.5% by mass, from 0.05 to 1% by mass, from 0.1 to 5% by mass, from 0.1 to 2.5% by mass and from 0.1 to 1% by mass.

The content of arginine in the drug (including quasi drug) is not particularly limited, but is, in terms of free form of arginine, preferably 0.01% by mass or more, more preferably 0.05% by mass or more and still more preferably 0.1% by mass or more, and preferably 10% by mass or less, more preferably 5% by mass or less, still more preferably 2.5% by mass or less and further preferably 1% by mass or less. Examples of the content also include from 0.01 to 10% by mass, from 0.01 to 5% by mass, from 0.01 to 2.5 mass %, from 0.01 to 1% by mass, from 0.05 to 10% by mass, from 0.05 to 5% by mass, from 0.05 to 2.5% by mass, from 0.05 to 1% by mass, from 0.1 to 10% by mass, from 0.1 to 5% by mass, from 0.1 to 2.5% by mass and from 0.1 to 1% by mass.

The content of arginine in the food and beverage is not particularly limited, but is, in terms of free form of arginine, preferably 0.01% by mass or more, more preferably 0.05% by mass or more and still more preferably 0.1% by mass or more, and preferably 5% by mass or less, more preferably 2.5% by mass or less and still more preferably 1% by mass or less. Examples of the content also include from 0.01 to 5% by mass, from 0.01 to 2.5% by mass, from 0.01 to 1% by mass, from 0.05 to 5% by mass, from 0.05 to 2.5% by mass, from 0.05 to 1% by mass, from 0.1 to 5% by mass, from 0.1 to 2.5% by mass and from 0.1 to 1% by mass.

In the present invention, the dosages and dosing regimens of catechins, citrulline and arginine may be appropriately determined by those skilled in the art according to the species, body weight, sex, age, condition or other factors of the particular subject. When orally administered, examples of the daily dosages per adult of the catechins, citrulline and arginine according to the present invention are as follows without being limited to:

[catechins] preferably from 100 to 3,000 mg/60 kg body weight, more preferably from 250 to 2,000 mg/60 kg body weight, and still more preferably from 250 to 1,000 mg/60 kg body weight; and

[citrulline (in terms of free form)] preferably from 100 to 3,000 mg/60 kg body weight, more preferably from 250 to 2,000 mg/60 kg body weight, and still more preferably from 250 to 1,000 mg/60 kg body weight; and [arginine (in terms of free form)] preferably from 100 to 3,000 mg/60 kg body weight, more preferably from 250 to 2,000 mg/60 kg body weight, and still more preferably from 250 to 1,000 mg/60 kg body weight. The above dosage is preferably administered once a day, or in divided doses twice or three or more times a day.

In the present invention, citrulline and arginine are used in the mass ratio of citrulline to arginine (in terms of free forms) of preferably from 1: 0.5 to 1:2 and more preferably from 1: 0.8 to 1:1.2. For example, the mass ratio of citrulline to arginine comprised in the ammonia metabolism promoting agent, endurance enhancing agent and anti-fatigue agent of the present invention is preferably from 1:0.5 to 1:2 and more preferably from 1:0.8 to 1:1.2, respectively. In a method for promoting ammonia metabolism, enhancing endurance or anti-fatigue of the present invention, citrulline and arginine are administered in the mass ratio of citrulline to arginine of preferably from 1:0.5 to 1:2 and more preferably from 1:0.8 to 1:1.2.

The mass ratio of the catechins to the total amount of citrulline and arginine (in terms of free forms) to be used in the present invention is preferably from 1:0.1 to 1:10, more preferably from 1:0.2 to 1:8, still more preferably from 1:0.5 to 1:2 and further preferably from 1:0.8 to 1:1.2. For example, the mass ratio of the catechins to the total amount of citrulline and arginine comprised in the ammonia metabolism promoting agent, endurance enhancing agent and anti-fatigue agent of the present invention is preferably from 1:0.1 to 1:10, more preferably from 1:0.2 to 1:8, still more preferably from 1:0.5 to 1:2 and further preferably from 1:0.8 to 1:1.2. For example, the dosage ratio by mass of the catechins to the total amount of citrulline and arginine to be administered in the method for promoting ammonia metabolism, enhancing endurance or anti-fatigue of the present invention is preferably from 1:0.1 to 1:10, more preferably from 1:0.2 to 1:8, still more preferably from 1:0.5 to 1:2 and further preferably from 1:0.8 to 1:1.2.

The present invention also includes the following substances, production methods, uses, methods and the like as exemplary embodiments. However, the present invention is not limited to these embodiments.

[1] An ammonia metabolism promoting agent, comprising catechins as an active ingredient.

[2] An agent for preventing or ameliorating hyperammonemia, comprising catechins as an active ingredient.

[3] An agent for preventing or ameliorating hepatic encephalopathy, comprising catechins as an active ingredient.

[4] An agent for preventing or ameliorating chronic fatigue syndrome, comprising catechins as an active ingredient.

[5] Use of catechins for producing an ammonia metabolism promoting agent.
[6] Use of catechins for producing an agent for preventing or ameliorating hyperammonemia.
[7] Use of catechins for producing of an agent for preventing or ameliorating hepatic encephalopathy.
[8] Use of catechins for producing an agent for preventing or ameliorating chronic fatigue syndrome.
[9] Use of catechins for promotion of ammonia metabolism.
[10] Use of catechins for preventing or ameliorating hyperammonemia.
[11] Use of catechins for preventing or ameliorating hepatic encephalopathy.
[12] Use of catechins for preventing or ameliorating chronic fatigue syndrome.
[13] Catechins for use in promotion of ammonia metabolism.
[14] Catechins for use in preventing or ameliorating hyperammonemia.
[15] Catechins for use in preventing or ameliorating hepatic encephalopathy.
[16] Catechins for use in preventing or ameliorating chronic fatigue syndrome.
[17] A method for promoting ammonia metabolism in a subject in need thereof, comprising administering an effective amount of catechins to the subject.
[18] A method for preventing or ameliorating hyperammonemia in a subject in need thereof, comprising administering an effective amount of catechins to the subject.
[19] A method for preventing or ameliorating hepatic encephalopathy in a subject in need thereof, comprising administering an effective amount of catechins to the subject.
[20] A method for preventing or ameliorating chronic fatigue syndrome in a subject in need thereof, comprising administering an effective amount of catechins to the subject.
[21] In [1] to [20], the amount per day per adult of the catechins to be used is preferably from 100 to 3,000 mg/60 kg body weight, more preferably from 250 to 2,000 mg/60 kg body weight and still more preferably from 250 to 1,000 mg/60 kg body weight.
[22] In [21], the above amount of the catechins is preferably administered once a day, or in divided amounts twice or three or more times a day.
[23] An ammonia metabolism promoting food or drink, comprising catechins as an active ingredient.
[24] An ammonia metabolism promoting food or drink according to [23], which is preferably a food or drink for suppression of central fatigue, suppression of sleepiness or suppression of malaise.
[25] In [1] to [24],
preferably, the catechins is at least one selected from the group consisting of catechin, gallocatechin, catechin gallate, gallocatechin gallate, epicatechin, epigallocatechin, epicatechin gallate and epigallocatechin gallate;
more preferably, the catechins comprises at least one selected from the group consisting of catechin gallate, epigallocatechin and epicatechin gallate;
still more preferably, the catechins comprises at least one selected from the group consisting of catechin gallate and epigallocatechin;
further preferably, the catechins is at least one selected from the group consisting of catechin gallate, epigallocatechin and epicatechin gallate; and
still further preferably, the catechins is at least one selected from the group consisting of catechin gallate and epigallocatechin, and/or
the tea extract comprising the catechins is used as the catechins.
[26] An ammonia metabolism promoting agent, comprising catechins, citrulline and arginine as active ingredients.
[27] An endurance enhancing agent, comprising catechins, citrulline and arginine as active ingredients.
[28] An anti-fatigue agent, comprising catechins, citrulline and arginine as active ingredients.
[29] An agent for preventing or ameliorating hyperammonemia, comprising catechins, citrulline and arginine as active ingredients.
[30] An agent for preventing or ameliorating hepatic encephalopathy, comprising catechins, citrulline and arginine as active ingredients.
[31] An agent for preventing or ameliorating chronic fatigue syndrome, comprising catechins, citrulline and arginine as active ingredients.
[32] Use of catechins, citrulline and arginine for producing an ammonia metabolism promoting agent.
[33] Use of catechins, citrulline and arginine for producing an endurance enhancing agent.
[34] Use of catechins, citrulline and arginine for producing an anti-fatigue agent.
[35] Use of catechins, citrulline and arginine for producing an agent for preventing or ameliorating hyperammonemia.
[36] Use of catechins, citrulline and arginine for producing an agent for preventing or ameliorating hepatic encephalopathy.
[37] Use of catechins, citrulline and arginine for producing an agent for preventing or ameliorating chronic fatigue syndrome.
[38] Use of catechins, citrulline and arginine for promotion of ammonia metabolism.
[39] Use of catechins, citrulline and arginine for endurance enhancement.
[40] Use of catechins, citrulline and arginine for anti-fatigue.
[41] Use of catechins, citrulline and arginine for preventing or ameliorating hyperammonemia.
[42] Use of catechins, citrulline and arginine for preventing or ameliorating hepatic encephalopathy.
[43] Use of catechins, citrulline and arginine for preventing or ameliorating chronic fatigue syndrome.
[44] A composition comprising catechins, citrulline and arginine for use in promotion of ammonia metabolism.
[45] A composition comprising catechins, citrulline and arginine for use in endurance enhancement.
[46] A composition comprising catechins, citrulline and arginine for use in anti-fatigue.
[47] A composition comprising catechins, citrulline and arginine for use in preventing or ameliorating hyperammonemia.
[48] A composition comprising catechins, citrulline and arginine for use in preventing or ameliorating hepatic encephalopathy.
[49] A composition comprising catechins, citrulline and arginine for use in preventing or ameliorating chronic fatigue syndrome.
[50] A method for promoting ammonia metabolism in a subject in need thereof, comprising administering effective amounts of catechins, citrulline and arginine to the subject.
[51] A method for enhancing endurance in a subject in need thereof, comprising administering effective amounts of catechins, citrulline and arginine to the subject.

[52] A method for anti-fatigue in a subject in need thereof, comprising administering effective amounts of catechins, citrulline and arginine to the subject.
[53] A method for preventing or ameliorating hyperammonemia in a subject in need thereof, comprising administering effective amounts of catechins, citrulline and arginine to the subject.
[54] A method for preventing or ameliorating hepatic encephalopathy in a subject in need thereof, comprising administering effective amounts of catechins, citrulline and arginine to the subject.
[55] A method for preventing or ameliorating chronic fatigue syndrome in a subject in need thereof, comprising effective amounts of catechins, citrulline and arginine to the subject.
[56] An ammonia metabolism promoting food and beverage, comprising catechins, citrulline and arginine as active ingredients.
[57] An endurance enhancing food and beverage, comprising catechins, citrulline and arginine as active ingredients.
[58] An anti-fatigue food and beverage, comprising catechins, citrulline and arginine as active ingredients.
[59] A food and beverage for preventing or ameliorating hyperammonemia, comprising catechins, citrulline and arginine as active ingredients.
[60] A food and beverage for preventing or ameliorating hepatic encephalopathy, comprising catechins, citrulline and arginine as active ingredients.
[61] A food and beverage for preventing or ameliorating chronic fatigue syndrome, comprising catechins, citrulline and arginine as active ingredients.
[62] In [26] to [61],
preferably, the catechins is at least one selected from the group consisting of catechin, gallocatechin, catechin gallate, gallocatechin gallate, epicatechin, epigallocatechin, epicatechin gallate and epigallocatechin gallate;
more preferably, the catechins comprises at least one selected from the group consisting of catechin gallate, epigallocatechin and epicatechin gallate;
still more preferably, the catechins comprises at least one selected from the group consisting of catechin gallate and epigallocatechin;
further preferably, the catechins is at least one selected from the group consisting of catechin gallate, epigallocatechin and epicatechin gallate; and
still further preferably, the catechins is at least one selected from the group consisting of catechin gallate and epigallocatechin,
and/or
the tea extract comprising the catechins is used as the catechins.
[63] In [26] to [62], the mass ratio of the catechins to the total amount of the citrulline and the arginine is preferably from 1:0.1 to 1:10, more preferably from 1:0.2 to 1:8, still more preferably from 1:0.5 to 1:2 and further preferably from 1:0.8 to 1:1.2.
[64] In [26] to [63], the mass ratio of the citrulline to the arginine is preferably from 1:0.5 to 1:2 and more preferably from 1:0.8 to 1:1.2.
[65] In [26] to [64],
the amounts per day per adult of the catechins, citrulline and arginine to be used are as follows:
[catechins] preferably from 100 to 3,000 mg/60 kg body weight, more preferably from 250 to 2,000 mg/60 kg body weight, and still more preferably from 250 to 1,000 mg/60 kg body weight;
[citrulline (in terms of free form)] preferably from 100 to 3,000 mg/60 kg body weight, more preferably from 250 to 2,000 mg/60 kg body weight, and still more preferably from 250 to 1,000 mg/60 kg body weight; and
[arginine (in terms of free form)] preferably from 100 to 3,000 mg/60 kg body weight, more preferably from 250 to 2,000 mg/60 kg body weight, and still more preferably from 250 to 1,000 mg/60 kg body weight.
[66] In [65], the above amounts of the catechins, citrulline and arginine are administered once a day, or in divided amounts twice or three or more times a day.

EXAMPLES

Hereinafter, the present invention will be more specifically described with reference to examples. However, the technical scope of the present invention is not limited to these examples.

Example 1

Effect of Catechins on Ammonia Metabolism of Primary Cultured Hepatocytes (Preparation of Primary Cultured Hepatocyte)
Each of mice (male Balb/c, 18 weeks old; Orientalbio Co., Ltd. was subjected to laparotomy under general anesthesia, infused via the portal vein through a peristaltic pump at a rate of 2 mL/min with Liver perfusion medium (Invitrogen) warmed at 37° C., and systemically perfused for 15 minutes. Subsequently, the mouse was similarly perfused with a liver digest medium for 15 minutes. Thereafter, the liver was removed, sliced thinly with a scissors, and passed through a filter (BD falcon) to dissociate it into cells. The cells were collected in a 50 mL tube, and were subjected to pipetting washing with 10 mL of Complete DMEM (D6046, Sigma), and were then centrifuged at 400 rpm and 4° C. for 3 minutes. The same operation was repeated three times to remove dead cells. Thereafter, the cells were suspended in a FBS free culture medium and seeded at $10^5$ cells/well in a 24-well plate. After culturing under the conditions of 37° C. and 5 volume % of $CO_2$ for 24 hours, the medium was changed and subjected to the following experiment.
(Catechin Stimulation and Quantitative Determination of Urea)
The cells 24 hours after seeding were washed twice with PBS. Thereafter, the medium was replaced with an arginine, leucine free DMEM medium (D9443, Sigma), and 10 μM of tea catechins (POLYPHENON 70S, Mitsui Norin Co., Ltd.) or water as a control was added to the medium. The cells were cultured under the conditions of 37° C. and 5 volume % of $CO_2$ for 24 hours, and the culture supernatant was then collected. Urea contained in the culture supernatant was quantitatively determined with QuantiChrom Urea Assay Kit (BioAssay Systems). Catechins composition of tea: GC 6.1 mass %, EGC 20.0 mass %, C 1.8 mass %, EC 7.9% by mass, EGCg 32.3 mass %, GCg 3.2% by mass, ECg 8.8% by mass and Cg 0.8% by mass.
(Gene Expression Profiling)
The cells were collected from the culture medium, RNA was extracted with RNeasy Mini Kit (QIAGEN), and cDNA synthesis was performed with High-Capacity RNA-to-cDNA Kit (Applied Biosystems). Thereafter, gene expression of each of the following ammonia metabolism related factors was quantitatively determined by real-time PCR (Taqman gene expression, Applied Biosystems):

CPS1: carbamoyl phosphate synthase-1 (Mm01256489 m1);

Otc: ornithine transcarbamoylase (Mm00493267_m1); and

Arg1: arginase-1 (Mm00475988_m1).

The results of quantitative determination of urea are shown in FIG. 1, and the results of gene expression profiling are shown in FIG. 2. The amount of urea production was statistically significantly increased and expressions of CPS1, Otc and Arg1 were statistically significantly enhanced in the catechin-stimulated group as compared to the control group.

Example 2

Effects of Catechin Species on Ammonia Metabolism of Primary Hepatocytes in Mice For cells, a hepatocyte culture kit (derived from a 10-week-old male Balb/c mouse, 24 wells, $1\times10^5$ cells/well, Cosmo Bio) was used. A final concentration of 5 mM of ammonium chloride (015-02991, Wako) and 1.4 µM or 4.2 µM of the following catechins (EGC, Cg or ECg) were added to a medium containing high glucose DMEM (31053028, Gibco) containing GlutaMAX (35050-061, Gibco), penicillin/streptomycin (168-23191, Wako) and ascorbic acid (014-04801, Wako), and the cells were cultured therein: EGC (NH020203, Nagara Science Co., Ltd.); Cg (NH 021302, Nagara Science Co., Ltd.); and ECg (NH 020302, Nagara Science Co., Ltd.). Cells cultured in a medium without any added catechins were used as a control. The culture supernatant was collected 24 hours later, and the ammonia contained therein was quantitatively determined using an ammonia assay kit (Abcam). The decrement in the ammonia amount in the culture medium 24 hour after addition of ammonium chloride and catechins relative to the ammonia amount at the time of addition was defined as an amount of change in ammonia in the culture medium.

The amount of change in ammonia in the culture medium is shown in Table 1. Each value in Table 1 represents the increasing rate of the amount of change in ammonia relative to that of the control. The statistical processing was performed by using multigroup comparison by Dunnett's test for n=4 per group (**: p <0.001, *: p<0.05). In the EGC 4.2 µM addition group and the Cg 4.2 µM addition group, the amount of change in ammonia in the culture medium significantly increases relative to the control, indicating that these catechin species have higher ammonia metabolism enhancing effect.

TABLE 1

|  | Ammonia change amount in culture medium Increasing rate relative to control (%) |
|---|---|
| Control | 100 |
| EGC 1.4 µM | 122 |
| EGC 4.2 µM | 186** |
| Cg 4.2 µM | 174* |
| ECg 4.2 µM | 126 |

Example 3

Effects of Catechins Ingestion on Ammonia Metabolism Related Enzyme Gene Expression in Liver (Animal and Tissue Collection)

Mice (male Balb/c, 6 weeks old; Orientalbio Co., Ltd.) were divided into two groups, each of which was fed with a control meal or a test meal (containing 0.5% catechins). During the test period, mice were fed ad libitum with the meal and water. Mice in each group were subjected to mild exercise running for 30 minutes a day (treadmill, 8 degrees slope; 15 m/min for 10 minutes→20 m/min for 30 minutes) four times a week. After 8 weeks, each mouse was dissected at rest and blood was collected from its abdominal vena cava. Thereafter, the liver was isolated and immediately frozen, and stored at −80° C.

TABLE 2

| Composition (% by mass) | Control meal | Test meal (containing 0.5% catechins) |
|---|---|---|
| Casein | 20 | 20 |
| Corn oil | 10 | 10 |
| Potato starch | 55.5 | 55 |
| Cellulose | 8.1 | 8.1 |
| AIN-76, mineral mixed | 4 | 4 |
| AIN-76, vitamin mixed | 2.2 | 2.2 |
| DL-methionine | 0.2 | 0.2 |
| Tea catechins * | 0 | 0.5 |
| Total amount | 100 | 100 |

* Tea catechins: POLYPHENON 70S (Mitsui Norin Co., Ltd.)
Composition: GG 6.1% by mass, EGC 20.0% by mass, C 1.8% by mass, EC 7.9% by mass, EGCg 32.3% by mass, GCg 3.2% by mass, ECg 8.8% by mass, Cg 0.8% by mass.

(Gene Expression Profiling)

The total RNA was extracted from the liver with RNeasy Mini Kit (QIAGEN). The cDNA was synthesized with High-Capacity RNA-to-cDNA Kit (Applied Biosystems). The gene expressions of the following ammonia metabolism related factors were quantitatively determined by real-time PCR (Taqman gene expression, Applied Biosystems).

NAGS: N-acetylglutamate synthase (Mm00467530_m1);

CPS1: carbamoyl phosphate synthase-1 (Mm01256489_m1);

Otc: ornithine transcarbamoylase (Mm00493267_m1);

ASS: argininosuccinate synthase (Mm00711256_m1);

ASL: argininosuccinate lyase (Mm01197741_m1); and

Arg1: arginase-1 (Mm00475988_m1).

The results are shown in FIG. 3. For all of the six genes examined, expressions were increased in the catechins-meal ingestion group as compared to the control group.

Example 4

Effect of Catechins Ingestion on Ammonia Metabolism in Liver (Animal and Tissue Collection)

Mice (male Balb/c, 8 weeks old; Orientalbio Co., Ltd.) were preliminarily bred for one week, and then divided into two groups so that the average values of initial endurance were equal between the two groups. Endurance was measured by a treadmill (8 degrees slope, 28 m/min) running. The mice in each group were subjected to mild exercise running (treadmill, 6 degrees slope, 20 m/min, 30 minutes) five times a week for a total of 4 weeks. One hour before each running exercise, any one of the following test substances was intragastrically administered to the mice in each group using an oral probe. Four weeks later, the test substance was orally administered to the mice in each group using an oral probe, and 1 hour later, each mouse was forced to perform treadmill running (8 degrees slope, 25 m/min) for 1 hour. Immediately after exercise, each mouse was dissected and blood was collected from its abdominal vena cava.

Thereafter, the liver was isolated and immediately frozen, and stored at −80° C.

Test substances
Control Group: water
Catechins administered group: Tea catechins* (0.2 g/kg body weight) ≠* Tea catechins: POLYPHENON 70S (Mitsui Norin Co., Ltd.; composition: GG 6.1% by mass, EGC 20% by mass, C 1.8% by mass, EC 7.9% by mass, EGCg 32.3% by mass, GCg 3.2% by mass, ECg 8.8% by mass, Cg 0.8% by mass.

(Quantitative Determination of Ammonia in Liver)

Ammonia in the liver was extracted and quantitatively determined with Ammonia Assay Kit (abcam 83360), and the amount of ammonia per liver weight was calculated.

The results are shown in FIG. 4. The amount of ammonia content in the liver was statistically significantly reduced in the catechins administered group as compared to the control group.

Example 5

Effect of Catechins Ingestion on Blood Ammonia Concentration

Mice were divided into two groups based on the same conditions in Example 4. A test substance was administered to each mouse and it was forced to perform exercise, and the blood was then collected. The blood ammonia concentration was measured for each of the collected blood sample. The blood ammonia concentration was measured with Ammonia/Ammonium Assay Kit (Abcam).

The results are shown in FIG. 5. The blood ammonia concentration was statistically significantly reduced in the catechins administered group as compared to the control group.

Reference Example

Effects of Citrulline and Arginine on Urea Production of Hepatocytes (Collection of Primary Cultured Hepatocytes)

Cells were recovered from the liver of each mouse and dead cells were removed, in the same procedure as in Example 1. Thereafter, cells were suspended in a DMEM medium, seeded at $10^5$ cells/well in a 24-well plate, and cultured.

(Quantitative Determination of Urea)

The cells 24 hours after seeding were washed twice with PBS. Thereafter, the medium was replaced with an FBS, arginine, leucine free DMEM medium (D9443, Sigma), and 5 mM of ammonium chloride (control), ammonium chloride+0.5 mM of L-arginine+0.5 mM of L-citrulline (Arg+Cit), or ammonium chloride+1 mM of L-citrulline (Cit) was added thereto. The culture supernatant was collected 24 hours later, and the urea contained therein was quantitatively determined with QuantiChrom Urea Assay Kit (BioAssay Systems).

The results of quantitative determination of urea are shown in FIG. 6. In both of the arginine+citrulline addition group (Arg+Cit) and the citrulline alone addition group (Cit), the amount of urea production by hepatocytes significantly increased, indicating that ammonia metabolism was enhanced.

Example 6

Effect of Catechins, Citrulline and Arginine on Endurance

Mice (male Balb/c, 8 weeks old; Orientalbio Co., Ltd.) were preliminarily bred for one week, and then divided into four groups so that the average values of initial endurance were equal in the four groups. During the test period, mice were fed ad libitum with a test meal (AIN 76-based powder meal (10% lipid)) and water. Endurance was measured by a treadmill (8 degrees slope, 28 m/min) running. The mice in each group were subjected to mild exercise running (treadmill, 6 degrees slope, 20 m/min, 30 minutes) five times a week for a total of 4 weeks. One hour before each running exercise, any one of the following test substances was intragastrically administered to the mice in each group using an oral probe. Four weeks later, endurance of each individual was measured again on a treadmill (8 degrees slope, 28 m/min).

Test substances
Group 1 (control): water
Group 2 (Cat): Tea catechins * (0.1 g/kg body weight)
Group 3 (Cat+Arg/Cit): Tea catechins * (0.1 g/kg body weight)+L-arginine (0.1 g/kg body weight)+L-citrulline (0.1 g/kg body weight)
Group 4 (Cat+Cit): Tea catechins * (0.1 g/kg body weight)+L-citrulline (0.2 g/kg body weight)
* Tea catechins: POLYPHENON 708 (Mitsui Norin Co., Ltd.; composition: GG 6.1% by mass, EGC 20% by mass, C 1.8% by mass, EC 7.9% by mass, EGCg 32.3% by mass, GCg 3.2% by mass, ECg 8.8% by mass, Cg 0.8% by mass)

The treadmill running time for the mice in each group is shown in FIG. 7. The running time was significantly prolonged in the group in which three components of catechins, arginine and citrulline were added (Cat+Arg/Cit), as compared to the catechins alone addition group (Cat) or the catechins+citrulline addition group (Cat+Cit), indicating that endurance was enhanced.

Example 7

Effects of Catechins, Citrulline and Arginine on Blood Ammonia Concentration

Mice (male Balb/c, 8 weeks old; Orientalbio Co., Ltd.) were preliminarily bred for one week, and then divided into three groups so that the average values of initial endurance were equal in the three groups. During the test period, mice were fed ad libitum with a test meal (AIN 76-based powder meal (10% lipid)) and water. Endurance was measured by a treadmill (8 degrees slope, 28 m/min) running. The mice in each group were subjected to mild exercise running (treadmill, 6 degrees slope, 20 m/min) five times a week for a total of 4 weeks. One hour before each running exercise, any one of the following test substances was intragastrically administered to the mice in each group using an oral probe. Four weeks later, the test substance was intragastrically administered to the mice in each group using an oral probe. One hour later each mouse was forced to perform treadmill running for 1 hour (8 degrees slope, 25 m/min), immediately thereafter blood was collected from its abdominal vena cava, and the blood ammonia concentration was measured. The blood ammonia concentration was measured with Ammonia/Ammonium Assay Kit (Abcam).

Test substances

Group 1 (control): water

Group 2 (Cat): Tea catechins * (0.2 g/kg body weight) Group 3 (Cat+Arg/Cit): Tea catechins * (0.2 g/kg body weight)+arginine (0.2 g/kg body weight)+citrulline (0.2 g/kg body weight)

* Tea catechins: POLYPHENON 70S (Mitsui Norin Co., Ltd.; composition: GG 6.1% by mass, EGC 20% by mass, C 1.8% by mass, EC 7.9% by mass, EGCg 32.3% by mass, GCg 3.2% by mass, ECg 8.8% by mass, Cg 0.8% by mass)

The blood ammonia concentration for the mice in each group is shown in FIG. 8. The blood ammonia concentration was significantly reduced in the group in which three components of catechins, arginine and citrulline were added (Cat+Arg/Cit), as compared to the catechins alone addition group (Cat).

What is claimed is:

1. A method for promoting ammonia metabolism in a subject in need thereof, comprising administering an effective amount of catechins to the subject, thereby increasing the subject's hepatic urea production and decreasing the subject's blood ammonia concentration.

2. The method of claim 1, wherein the subject is in need of ameliorating hyperammonemia.

3. The method of claim 1, wherein the subject is in need of ameliorating hepatic encephalopathy.

4. A method for ameliorating chronic fatigue syndrome in a subject in need thereof, comprising administering an effective amount of catechins to the subject, wherein the effective amount increases the subject's hepatic urea production and decreases the subject's blood ammonia concentration, thereby ameliorating the subject's chronic fatigue syndrome, wherein the fatigue is caused by ammonia accumulation.

5. A method for promoting ammonia metabolism in a subject in need thereof, comprising administering an effective amounts of catechins, citrulline and arginine to the subject, wherein the effective amount increases the subject's hepatic urea production and decreases the subject's blood ammonia concentration, thereby promoting the subject's ammonia metabolism.

6. A method for enhancing endurance in a subject in need thereof, comprising administering effective amounts of catechins, citrulline and arginine to the subject, wherein the effective amount increases the subject's hepatic urea production and decreases the subject's blood ammonia concentration, thereby enhancing the subject's endurance.

7. A method for anti-fatigue in a subject in need thereof, comprising administering effective amounts of catechins, citrulline and arginine to the subject, wherein the effective amount increases the subject's hepatic urea production and decreases the subject's blood ammonia concentration, thereby having an anti-fatigue effect in the subject.

8. The method according to claim 5, wherein the mass ratio of the catechins to the total amount of citrulline and arginine is from 1:0.1 to 1:10.

9. The method according to claim 5, wherein the mass ratio of citrulline to arginine is from 1:0.5 to 1:2.

10. The method according to claim 6, wherein the mass ratio of the amount of catechins to the total amount of citrulline and arginine is from 1:0.1 to 1:10.

11. The method according to claim 6, wherein the mass ratio of citrulline to arginine is from 1:0.5 to 1:2.

12. The method according to claim 7, wherein the mass ratio of the amount of catechins to the total amount of citrulline and arginine is from 1:0.1 to 1:10.

13. The method according to claim 7, wherein the mass ratio of citrulline to arginine is from 1:0.5 to 1:2.

14. The method according to claim 8, wherein the mass ratio of citrulline to arginine is from 1:0.5 to 1:2.

15. The method according to claim 10, wherein the mass ratio of citrulline to arginine is from 1:0.5 to 1:2.

16. The method according to claim 12, wherein the mass ratio of citrulline to arginine is from 1:0.5 to 1:2.

* * * * *